United States Patent
Strand et al.

(10) Patent No.: US 12,194,129 B2
(45) Date of Patent: *Jan. 14, 2025

(54) LEAVE-ON ORAL CARE COMPOSITIONS

(71) Applicant: The Procter & Gamble Company, Cincinnati, OH (US)

(72) Inventors: Ross Strand, Singapore (SG); Yang Su, Beijing (CN); Yunming Shi, Beijing (CN); Thanigaivel Shanmugam, Beijing (CN); Guannan Wang, Beijing (CN); Xiaoxiao Li, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/530,533

(22) Filed: Dec. 6, 2023

(65) Prior Publication Data

US 2024/0099957 A1    Mar. 28, 2024

Related U.S. Application Data

(63) Continuation of application No. 16/899,882, filed on Jun. 12, 2020, now Pat. No. 11,883,520.

(30) Foreign Application Priority Data

Jun. 14, 2019  (WO) ................ PCT/CN2019/091294
Jun. 11, 2020  (WO) ................ PCT/CN2020/095575

(51) Int. Cl.
| | | |
|---|---|---|
| A61K 8/73 | (2006.01) | |
| A61K 8/04 | (2006.01) | |
| A61K 8/49 | (2006.01) | |
| A61K 8/81 | (2006.01) | |
| A61Q 11/00 | (2006.01) | |

(52) U.S. Cl.
CPC .............. *A61K 8/735* (2013.01); *A61K 8/042* (2013.01); *A61K 8/4946* (2013.01); *A61K 8/8147* (2013.01); *A61Q 11/00* (2013.01); *A61K 2800/30* (2013.01); *A61K 2800/87* (2013.01); *A61K 2800/92* (2013.01)

(58) Field of Classification Search
CPC ...... A61K 8/735; A61K 8/042; A61K 8/4986; A61K 8/8147; A61K 2800/87; A61K 2800/92; A61Q 11/00
See application file for complete search history.

(56) References Cited

U.S. PATENT DOCUMENTS

| | | | |
|---|---|---|---|
| 5,876,744 A | 3/1999 | Della et al. | |
| 6,592,884 B2 | 7/2003 | Hofmann et al. | |
| 9,320,699 B2 | 4/2016 | Porter et al. | |
| 9,532,939 B2 | 1/2017 | Ripley et al. | |
| 10,383,796 B2 | 8/2019 | Truitt | |
| 11,883,520 B2 * | 1/2024 | Strand ................... | A61K 8/735 |
| 2002/0028241 A1 | 3/2002 | Foreman et al. | |
| 2004/0037789 A1 | 2/2004 | Moneuze | |
| 2005/0142076 A1 | 6/2005 | Fukunaga et al. | |
| 2006/0286044 A1 | 12/2006 | Robinson | |
| 2007/0003502 A1 | 1/2007 | Tanabe et al. | |
| 2007/0237726 A1 | 10/2007 | White et al. | |
| 2007/0298087 A1 | 12/2007 | Biegajski | |
| 2009/0068122 A1 | 3/2009 | Pilch | |
| 2011/0104081 A1 | 5/2011 | Scott | |
| 2012/0014883 A1 | 1/2012 | Scott | |
| 2012/0082630 A1 | 4/2012 | Haught | |
| 2012/0202767 A1 | 8/2012 | Di Schiena | |
| 2013/0017238 A1 | 1/2013 | Porter et al. | |
| 2013/0171221 A1 | 7/2013 | Deng | |
| 2014/0242005 A1 | 8/2014 | Koumans | |
| 2018/0333349 A1 | 11/2018 | Ansari et al. | |
| 2019/0021966 A1 | 1/2019 | Jha et al. | |
| 2020/0054667 A1 | 2/2020 | Mevorat Kaplan et al. | |
| 2020/0390676 A1 | 12/2020 | Strand | |
| 2020/0390677 A1 | 12/2020 | Strand | |
| 2020/0390801 A1 | 12/2020 | Strand | |

FOREIGN PATENT DOCUMENTS

| | | |
|---|---|---|
| CN | 101415731 A | 4/2009 |
| CN | 102125507 A | 7/2011 |
| CN | 105213298 A | 1/2016 |
| CN | 105434315 A | 3/2016 |
| CN | 106963727 A | 7/2017 |
| CN | 107432853 A | 12/2017 |
| CN | 107468553 A | 12/2017 |
| CN | 107496195 A | 12/2017 |
| CN | 107536725 A | 1/2018 |
| CN | 108324739 A | 7/2018 |
| CN | 108888770 A | 11/2018 |
| CN | 108939079 A | 12/2018 |

(Continued)

OTHER PUBLICATIONS

All Office Actions; U.S. Appl. No. 18/390,158, filed Dec. 20, 2023.
U.S. Appl. No. 18/390,158, filed Dec. 20, 2023, to Ross Strand et al.
All Office Actions; U.S. Appl. No. 16/899,834, filed Jun. 12, 2020.
All Office Actions; U.S. Appl. No. 16/899,882, filed Jun. 12, 2020.
All Office Actions; U.S. Appl. No. 16/899,919, filed Jun. 12, 2020.
All Office Actions; U.S. Appl. No. 18/519,251, filed Nov. 27, 2023.
Dahiya P, Kamal R. Hyaluronic acid: A boon in periodontal therapy. North Am J Med Sci 2013; 5:309-15. (Year: 2013).
Database GNPD [Online] Mintel; Anonymous: "Gengigel Oral Hygiene Range", XP055809999, Database accession No. 341172, Feb. 17, 2005.

(Continued)

*Primary Examiner* — Michael P Cohen
(74) *Attorney, Agent, or Firm* — Elizabeth A. Conklin

(57) ABSTRACT

Leave-on oral care compositions having good spreadability and improved retention property are provided for promoting Gum Health of a user. Leave-on oral care compositions can comprise a hyaluronic acid or a salt thereof, a polyacrylic acid as a mucoadhesive polymer, and an additional polymer.

20 Claims, No Drawings

(56) References Cited

FOREIGN PATENT DOCUMENTS

| | | | |
|---|---|---|---|
| CN | 109010471 A | 12/2018 | |
| CN | 109528805 A | 3/2019 | |
| CN | 109820821 A | 5/2019 | |
| CN | 110123702 A | 8/2019 | |
| DE | 102017005168 A1 | 12/2018 | |
| EP | 2666517 A1 | 11/2013 | |
| EP | 3056195 A1 | 8/2016 | |
| JP | H08500578 A | 1/1996 | |
| JP | 2002029950 A | 1/2002 | |
| JP | 2004012747 A1 | 1/2004 | |
| JP | 2009274967 A | 11/2009 | |
| JP | 2010511053 A | 4/2010 | |
| JP | 2010138080 A | 6/2010 | |
| JP | 2012153677 A | 8/2012 | |
| JP | 2014501733 A | 1/2014 | |
| JP | 2015189708 A | 11/2015 | |
| JP | 2017523993 A | 8/2017 | |
| JP | 2018002719 A | 1/2018 | |
| JP | 6519930 B2 | 5/2019 | |
| KR | 100794264 B1 | 1/2008 | |
| KR | 100805635 B1 | 2/2008 | |
| WO | 2016112998 A1 | 7/2016 | |
| WO | 2018212771 A1 | 11/2018 | |
| WO | 2019025599 A1 | 2/2019 | |

OTHER PUBLICATIONS

Database GNPD [Online] Mintel; Anonymous: "Travel Kit", XP055729622, Database accession No. 6318883, Feb. 12, 2019.

Google patent search hyaluronic polyacrylic water, Retrieved from: https://patents.google.com/?q=hyaluronic+polyacrylic+water&oq=hyaluronic+polyacrylic+water, Retrieved on Jun. 29, 2021, 2 Pages.

Google scholar search hyaluronic polyacrylic mucoadhesive, Retrieved from: https://scholar.google.com/scholar?hl=en&as_sdt=0%2C5&q=hyaluronic+polyacrylic+mucoadhesive&btnG=, Retrieved on Jun. 29, 2021, 2 Pages.

Google search hyaluronic polyacrylic mucoadhesive, Retrieved from: https://www.google.com/search?q=hyaluronic_polyacrylic_mucoadhesive&rlz=1C1GCEA_enIN879IN879&oq=hyaluronic_polyacrylic_mucoadhesive&aqs=chrome..69i57.1423j0j15&sourceid=chrome&ie=UTF-8, Retrieved on Jun. 29, 2021, 2 Pages.

Google search polyvinylpyrrolidone mucoadhesive properties hyaluronic acid polyacrylic, Retrieved from: https://www.google.com/search?q=polyvinylpyrrolidone+mucoadhesive+properties+hyaluronic+acid+polyacrylic&rlz=1C1GCEA_enIN879IN879&oq=polyvinylpyrrolidone+mucoadhesive+properties+hyaluronic+acid+polyacrylic&aqs=chrome..69i57.505j0j15&sourceid=chrome&ie=UTF-8, Retrieved on Jun. 29, 2021, 2 Pages.

PCT Search Report and Written Opinion for PCT/CN2020/095575 dated Sep. 9, 2021, 12 pages.

PCT Search Report and Written Opinion for PCT/CN2019/091294 dated Mar. 13, 2020, 9 pages.

PCT Search Report and Written Opinion for PCT/CN2020/095575 dated Sep. 15, 2020, 13 pages.

Roy et al., Polymers in Mucoadhesive Drug-Delivery Systems: A Brief Note, Designed monomers and polymers, vol. 12, Issue 6, Jan. 1, 2009, pp. 483-495.

U.S. Appl. No. 18/519,251, filed Nov. 27, 2023, to Ross Strand et al.

* cited by examiner

LEAVE-ON ORAL CARE COMPOSITIONS

FIELD OF THE INVENTION

The present invention relates to oral care compositions comprising a hyaluronic acid and a combination of polymers for promoting Gum Health of a user. In particular, such oral care compositions provide a leave-on formula having good spreadability which is helpful for improving gingival wound healing.

BACKGROUND OF THE INVENTION

Gum disease, such as gingivitis and/or periodontitis, gives rise to acute and chronic gum inflammation in the oral cavity. "Gingivitis" is the milder form of the disease. Symptoms of gingivitis may include: gingival bleeding; and redness, swollen, or tender gums. If left untreated, gingivitis can advance to "periodontitis". With periodontitis, gums pull away from the teeth and form spaces called " periodontal pockets" that can become infected by pathogenic bacteria. The bacteria are present on the tooth root surfaces as biofilms. The bacteria in the biofilms can attack the gingival and underlying alveolar bone supporting teeth. These attacks can cause major damage to the soft tissue and bone that support teeth. In the later stage of gum disease (i.e., "advanced periodontitis"), more serious problems of loosening of teeth and eventual tooth loss can occur.

Users having gum problems have typically been limited to brushing teeth with antibacterial toothpastes as a solution at home. This mechanism can help clean and control the plaque and bacteria and associated toxin challenge on the host. However, due to the limited residence time of brushing, 2 minutes, there is little time to repair, or even strengthen the host tissue. Accordingly, users expect a regimen that can be applied to the host tissue for a longer time and to repair, strengthen and rejuvenate the gum. In order to meet such user expectation, a number of gel or ointment products that can be applied to the oral cavity have been developed to provide such benefits. For example, a user can apply a gel formulation product onto oral tissue, e.g. gum area and leave for some time before expectorating or alternatively without expectorating or rinsing off. Desirable products require sufficient substantivity and rheological properties to enable application to the oral cavity, to adhere to the oral tissue and to release the contained oral care benefits agents over an extended period of time.

Therefore there is a continuous need to provide such leave-on composition which not only has a good spreadability and adhesion to provide good sensory benefits to users, but also provides desirable Gum Health benefits (e.g., gingival wound healing and anti-bacterial benefits) to users.

SUMMARY OF THE INVENTION

A novel technology for formulating a leave-on oral care composition is developed by the inventors to meet at least some of the needs described above. Particularly, it is a surprising discovery that a leave-on oral care composition comprising hyaluronic acid and combinations of polyacrylic acid and an additional polymer provides users with a desirable sensory feel and also good Gum Health benefits to the users, especially good gingival wound healing benefit.

Without being bound by any theory, it is believed that the leave-on oral care composition of the present invention, which exhibits improved wound healing benefit and barrier function benefit, may in turn help to relieve gingival pain, promote gingival regeneration, accelerate repairing of mucosal/gingival damage and healing of gingival bleeding wound, and/or enhancing gingival immunity/resistance. The leave-on oral care composition may further help forming a protective film over lesion and irritation caused by ill-fitting dentures. The leave-on oral care composition may further help repairing or healing of gingival damage post root scaling/planning or gum grafts. The leave-on oral care composition may even further to help improve hydration to the mucosal and even help alleviate or relieve dry mouth.

It is advantageous that the leave-on oral care composition has an optimal viscosity profile so to provide a good spreadability.

It is also advantageous that the leave-on oral care composition is not heavy, overly sticky/tacky and provide user enjoyable experiences, such as refreshing, safe, and effective feel.

It is further advantageous to provide users a pleasant mouth feel and taste for long term use, which is recognized as a balancing act between substantivity, adhesiveness and viscosity.

It is yet advantageous to apply the leave-on oral care composition after brushing teeth, or as the last step of oral hygiene regimen. It is advantageous that the leave-on oral care composition is applied on the soft tissue of the oral cavity, leaving for more than 2 minutes, preferably more than 10 minutes, and without being rinsed off or expectorated.

It is further advantageous to apply the leave-on gel to the gum by using a delivery carrier, wherein the delivery carrier may comprise strip, film of material, dental tray, aligner, sponge material, applicator, or mixtures thereof.

In one aspect, the present invention is directed to an oral care composition comprising: (a) from about 0.1% to about 10%, by weight of the composition, of a hyaluronic acid or a salt thereof; (b) from about 0.1% to about 10%, by weight of the composition, of a polyacrylic acid; and (c) from about 0.1% to about 10%, by weight of the composition, of an additional polymer. The additional polymer is preferably selected from natural gum, linear sulfated polysaccharide, anionic cellulose, nonionic cellulose derivative, co-polymers of maleic anhydride with methyl vinyl ether, polyvinyl pyrrolidine and combinations thereof. Preferably, the oral care composition is a leave-on composition. In one example, the oral care composition may further comprise from about 0.1% to about 5%, by weight of the composition, of allantoin.

Preferably, the hyaluronic acid has a weight average molecular weight of from about 900,000 Daltons to about 5,000,000 Daltons, preferably from about 900,000 Daltons to about 2,000,000 Daltons. More preferably, the hyaluronic acid is present in the amount of from about 0.1% to about 5%, more preferably from about 0.2% to about 0.8%, by weight of the composition.

In another aspect of the present invention, the above-mentioned oral care composition further comprises from about 30% to about 85%, preferably from about 40% to about 80%, preferably from about 45% to about 75%, by weight of the composition, of total water content. Preferably, the above-mentioned oral care composition is substantially free of abrasives, preferably essentially free of abrasives.

In yet another aspect of the present invention, there is provided a method of improving Gum Health of a subject using the oral care composition as defined therein, comprising the step of applying the oral care composition onto the intraoral tissue of the subject, on which the oral care composition is left on without removal for at least 1 minute, or at least 2 minutes, or for a duration of time from 1 minute to 1000 minutes, or from 2 minutes to 200 minutes; optionally the applying step can be conducted as the last step of an oral hygiene regimen.

In still another aspect of the present invention, there is provided a method of improving Gum Health of a subject, comprising at least two steps: (a) brushing teeth with a toothpaste, preferably an antibacterial toothpaste, more preferably a stannous-containing toothpaste, or even preferably a toothpaste containing a stannous ion source and an amino acid; and (b) consequently, preferably immediately, applying the oral are composition as defined herein onto the intraoral tissue of the subject, preferably applying along the gingival margin, sulcus or pockets, on which the oral care composition is left for a duration of time from 1 minute to 1000 minutes.

In yet still another aspect of the present invention, there is provided a kit comprising an oral care composition of the present invention and a delivery carrier, wherein the delivery carrier comprises strip, film of material, dental tray, aligner, sponge material, applicator, or mixtures thereof. In a preferred example, the kit comprises an oral care composition of the present invention and an applicator having a handle and a head. There is also provided a kit comprising a toothpaste and the oral care composition of the present invention. In an example, the kit comprises a toothpaste and the oral care composition of the present invention. In a preferred example, the kit comprises an antibacterial toothpaste and the oral care composition of the present invention, where the toothpaste is preferably a stannous-containing toothpaste, more preferably is a toothpaste comprising a stannous ion source and an amino acid. Preferably, the toothpaste and the oral care composition are respectively and sequentially applied to improve Gum Health.

These and other features of the present invention will become apparent to one skilled in the art upon review of the following detailed description when taken in conjunction with the appended claims.

DETAILED DESCRIPTION OF THE INVENTION

Definitions

As used herein, the articles including "a" and "an" when used in a claim, are understood to mean one or more of what is claimed or described.

The term "comprising" as used herein means that steps and ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, components, steps, or limitations described herein.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The term "gingival gel" or "gum gel" as used herein means a product or a composition is in a form of gel which intent to primarily applied to the gingival tissue, as well as other soft tissue (e.g. buccal mucosa) inside the oral cavity of a subject, preferably more than 50% of the product or composition is applied to the gingival and other soft tissue.

As used herein, "leave-on" means a product or a composition is adopted or applied onto a surface for a certain amount of time, e.g. more than one minute, preferably more than two minutes. Preferably, a "leave-on" gel means a gel product or composition which is intent not to be rinsed off or expectorated.

The term "Gum Care" means those benefits aiming to alleviate one or more symptoms of the earlier stage of gum disease (i.e., gingivitis), which includes: relief of red, swollen, or tender gums; and/or stem gum bleeding.

The term "Gum Health" as used herein refers to inherent or promoted benefits of an oral care composition to provide "Gum Care" benefits that include at least improve gingival wound healing, as well as, providing additional improve reduction of bacterial activity to mitigate the harmful effects of bacteria as it relates to gum disease, including gingivitis, periodontitis or both.

The term "promoting" as used herein means to promote and/or enhance the Gum Health benefits associated with using the oral care compositions of the present invention in the oral cavity.

The term "substantially free" as used herein refers to the presence of no more than 0.05%, preferably no more than 0.01%, and more preferably no more than 0.001%, of an indicated material in a composition, by total weight of such composition.

The term "essentially free" as used herein means that the indicated material is not deliberately added to the composition, or preferably not present at analytically detectable levels. It is meant to include compositions whereby the indicated material is present only as an impurity of one of the other materials deliberately added.

The term "total water content" as used herein means both free water and water that is bound by other ingredients in the oral care composition.

The term "oral hygiene regimen" or "regimen" can be for the use of two or more separate and distinct treatment steps for oral health, e.g. toothpaste, mouth rinse, floss, toothpicks, spray, water irrigator, massager.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified.

All measurements referred to herein are made at 25° C. (i.e., room temperature) unless otherwise specified.

Oral Care Compositions

The oral care composition described in the present invention is configured for applying on the gingival tissue, as well as other soft tissue (e.g. buccal mucosa) inside the oral cavity of a subject. It has been surprisingly discovered that the oral care composition of the present invention is useful for promoting Gum Health benefits to users, particularly is helpful for improving wound healing benefit.

In one aspect, the present invention is directed to an oral care composition which is in a gel form. The oral care composition comprises:

a) from about 0.1% to about 10%, by weight of the composition, of a hyaluronic acid or a salt thereof;

b) from about 0.1% to about 10%, by weight of the composition, of a polyacrylic acid;

c) from about 0.1% to about 10%, by weight of the composition, of an additional polymer selected from natural gum, linear sulfated polysaccharide, anionic cellulose, nonionic cellulose derivative, co-polymers of maleic anhydride with methyl vinyl ether, polyvinyl pyrrolidine and combinations thereof; and d) from more than about 30% to about 75%, by weight of the composition, of a total water content.

Preferably, the oral care composition further comprises from about 0.01% to about 5% of allantoin by weight of the composition. In some embodiment, the allantoin is present in the amount of from about 0.05% to about 4%, preferably from about 0.08% to about 3%, by weight of the composition.

The oral care composition described therein is a leave-on composition. It is desirable to have a gel having desired viscosity for use in the present invention that enables easy application, thin layer formation and evenly spread into gingival sulcus/pockets and along gingival gum line. The oral care composition of the present invention may have a viscosity profile with a consistency coefficient K of about 50 Pa·s to about 500 Pa·s, as measured by the Rheological Test Method described herein. Preferably, the oral care composition has a viscosity consistency coefficient K of about 50 Pa·s to about 250 Pa·s, preferably from about 50 Pa·s to about 200 Pa·s, more preferably from about 50 Pa·s to about 150 Pa·s. Such viscosity profile range provides better sensory experience of spreadability for a user. If a product is too viscous, it may be hard for a user to spread it evenly onto gingival tissue. If the product has a too low viscosity, it is runny and hard to be retained on appropriate area by finger or applicator.

In one aspect, the oral care composition of present invention has a desirable mucoadhesion property. Mucoadhesion can be defined as adhesive interaction between two surfaces where one is at least mucosa for a given period through interfacial forces with a consequent decreased in the surface energy. Mucoadhesion polymers for oral care application should ideally (1) easily retain hydrophilic and lipophilic active ingredients and not hinder their release; (2) promote active ingredient penetration and absorption, (3) adhere as quickly as possible to biological substrate and be retained for a period of time, (4) be safe, (5) be cost effective and (6) provide consumer acceptable application.

The oral care composition of present invention has a Mucoadhesion Index in the range of not less than 0.6 FI %, as measured by the Mucoadhesion Test Method described herein. Preferably, the oral care composition has a Mucoadhesion Index of no less than about 0.8 FI %, more preferably no less than about 1.0 FI %. Preferably, the oral care composition has a Mucoadhesion Index of less than about 20 FI %, preferably less than about 15 FI %, more preferably less than about 10 FI %. For instance, the oral care composition may have a Mucoadhesion Index of no less than about 1.2 FI %, or no less than about 1.3 FI %, or no less than about 1.5 FI %, or no less than about 1.8 FI %, or no less than about 2.0 FI %.

Hyaluronic Acid and Salts

The oral care composition of the present invention comprises a hyaluronic acid or a salt thereof. Hyaluronic acid is a polysaccharide present in the connective tissue of vertebrates, a polymer of glucuronic acid and n-acetyglucosylamine, and is a member of glucosamine family with a high molecular weight. Hyaluronic acid (Hyaluronan) is an indispensable component of intact, healthy gingiva, and oral mucosal tissue. It has many properties that make it a potentially ideal molecule for assisting wound healing by inducing early granulation tissue formation, inhibiting inflammation, promoting epithelial turnover and also connective tissue angiogenesis. Preferably, the hyaluronic acid used in the present invention has a weight average molecular weight (M.W.) of from about 900,000 Daltons to about 5,000,000 Daltons, preferably from about 900,000 Daltons to about 3,000,000 Daltons; more preferably from about 900,000 Daltons to about 2,000,000 Daltons. The molecular weight of the hyaluronic acid can be measured using Gel Electrophoresis method. The hyaluronic acid of the present invention is present in the amount of from about 0.1% to about 5.0% by weight of the composition. Preferably, the hyaluronic acid is present in the amount of from about 0.2% to about 2%, alternatively from about 0.2% to about 1%, more preferably from about 0.2% to about 0.8%, by weight of the composition. For example, the hyaluronic acid is present in the amount of about 0.2%, or about 0.3%, or about 0.4%, or about 0.5%, or about 0.6%, or about 0.7%, or about 0.8%, or about 0.9%, or about 1.0%, by weight of the composition. Any salt of the hyaluronic acid suitable for oral care product can be used in the present invention. Preferably, the hyaluronate salt may be sodium hyaluronate.

Allantoin

The oral care composition may further comprise from about 0.01% to about 5% of allantoin by weight of the composition. Allantoin, also called 5-ureidohydantoin or glyoxyldiureide, is an oxidation product of uric acid. Allantoin helps to heal wounds and skin irritations and stimulates the growth of healthy tissue. In some examples, the allantoin can be present in the amount of from about 0.02% to about 4%, or from about 0.05% to about 3%, by weight of the composition. For example, the allantoin can be present in the amount of about 0.05%, or about 0.1%, or about 0.2%, or about 0.3%, or about 0.4%, or about 0.5%, or about 0.6%, or about 0.8%, or about 0.9%, or about 1%, by weight of the composition. It is discovered that allantoin can help to improve or increase the wound healing benefit for the hyaluronic acid-containing composition.

Mucoadhesive Polymer

The oral care composition of the present invention comprises polyacrylic acid as a mucoadhesive polymer. Polyacrylic acid (PAA) polymer is a generic term for the synthetic high molecular weight polymers of acrylic acid. These may be homopolymers of acrylic acid, crosslinked with an allyl ether pentaerythritol, allyl ether of sucrose or allyl ether of propylene. And, in a water solution at neutral pH, PAA is an anionic polymer, i.e. many of the side chains of PAA will lose their protons and acquire a negative charge. This makes PAAs polyelectrolytes, with the ability to absorb and retain water and swell to many times their original volume. Polyacrylic acid is also called carbomer as tradename. For example, Carbopol®-type polymers, such as Carbopol®, Pemulen® and Noveon®, are polymers of acrylic acid, crosslinked with polyalkenyl ethers or divinyl glycol. Carbomer commercial codes, e.g. 940™, indicate the molecular weight and the specific components of the polymer.

Preferably, the polyacrylic acid used in the invention is present in the amount of from about 0.1% to about 10% by weight of the oral care composition. For example, the polyacrylic acid is present in the amount of from about 0.2% to about 5%, or from about 0.5% to about 8%, or from about 1.0% to about 5%, by weight of the oral care composition.

Additional Polymer

The oral care composition of the present invention comprises an additional polymer. Preferably the oral care composition comprises from about 0.1% to about 10%, preferably from about 0.5% to about 6%, more preferably from about 1% to about 5%, yet still more preferably from about 1.3% to about 2.6%, by weight of the composition, of the additional polymer. The additional polymer is selected from natural gum, linear sulfated polysaccharide, anionic cellulose, nonionic cellulose derivative, polyvinyl pyrrolidine, polymers comprising at least a polycarboxylated ethylene backbone, and combinations thereof.

Preferably, a natural gum is selected from the group consisting of gum karaya, gum arabic (also known as acacia gum), gum tragacanth, xanthan gum, and combination thereof. More preferably, the natural gum is xanthan gum. Xanthan gum is a polysaccharide secreted by the bacterium *Xanthomonas camestris*. Generally, xanthan gum is composed of a penta-saccharide repeat units, comprising glucose, mannose, and glucuronic acid in a molar ratio of 2:2:1, respectively. The chemical formula (of the monomer) is $C_{35}H_{49}O_{29}$. In one example, the xanthan gum is from CP Kelco Inc (Okmulgee, US).

Preferably, the linear sulfated polysaccharide is a carrageenan. Examples of carrageenan include Kappa-carrageenan, Iota-carrageenan, Lambda-carrageenan, and combinations thereof. In one example, the linear sulfated polysaccharide is Iota-carrageenan.

Preferably, the anionic cellulose is a carboxymethyl cellulose ("CMC"). In one example, the CMC is prepared from cellulose by treatment with alkali and monochloroacetic acid or its sodium salt. Different varieties are commercially characterized by viscosity. One commercially available example is Aqualon™ branded CMC from Ashland Special Ingredients (e.g., Aqualon™ 7H3SF; Aqualon™ 9M3SF; Aqualon™ TM9A; Aqualon™ TM12A).

Preferably, the nonionic cellulose or derivative thereof has a weight average molecular weight ranging from about 50,000 Daltons to about 1,300,000 Daltons, and preferably an average degree of polymerization from 300 to 4,800. More preferably, the nonionic cellulose or derivative thereof is hydroxyethyl cellulose ("HEC"). In other examples, the nonionic cellulose may be hydroxypropyl cellulose or hydroxymethyl cellulose.

Preferably, the polymer comprising at least a polycarboxylated ethylene backbone is selected from the group consisting of: co-polymers of maleic anhydride with methyl vinyl ether having a weight average molecular weight of 30,000 to 1,000,000 Daltons; homo-polymers of acrylic acid; and co-polymers of maleic acid and acrylic acid or methacrylic.

In an example, the GANTREZ™ series of polymers are co-polymers of maleic anhydride with methyl vinyl ether having a weight average molecular weight (M.W.) of 30,000 Daltons to 1,000,000 Daltons. These co-polymers are available for example as GANTREZ™ AN139 (M.W. 500,000 Daltons), AN119 (M.W. 250,000 Daltons) and S-97 Pharmaceutical Grade (M.W. 70,000 Daltons), from Ashland Chemicals (Kentucky, USA).

In another example, the ACUSOL™ and the SOKALAN series of polymers include homopolymers of acrylic acid and copolymers of maleic acid and acrylic acid or methacrylic. Examples are 0:1000 to 1000:0 copolymers of maleic acid with acrylic acid having a weight average molecular weight (M.W.) of about 2,000 to about 1,000,000. These copolymers are commercially available as ACUSOL™ 445 and 445N, ACUSOL™ 531, ACUSOLT™ 463, ACUSOL™ 448, ACUSOL™ 460, ACUSOL™ 465, ACUSOL™ 497, ACUSOL™ 490 from Dow Chemicals (Michigan, USA) and as Sokalan® CP 5, Sokalan® CP 7, Sokalan® CP 45, and Sokalan® CP 12 S from BASF (New Jersey, USA).

Preferably, the ratio between the mucoadhesive polymer and the additional polymer is from about 5:1 to about 1:5. In some examples, the ratio between the polyacrylic acid and the additional polymer can be from about 4:1 to about 1:4, alternatively from about 3:1 to about 1:3, alternatively from about 2.5:1 to about 1: 2.5. For example, the oral care composition of the present invention can comprise polyacrylic acid and polyvinyl pyrrolidine and the ratio between thereof is from about 3:1 to about 1:3, or about 2:1 to about 1:2, or about 1.5:1 to about 1: 1.5, or being about 1.2:1, or about 1:1, or any combinations between the above-mentioned values. In an alternative example, the oral care composition comprises a polyacrylic acid and hydroxyethyl cellulose the ratio of which being from about 3:1 to about 1:3, or from about 2:1 to about 1:2, or being about 1.5, or about 1.2, or about 1.

Water

The term "orally acceptable carrier" as used herein means a liquid or semi-solid vehicle such as a paste or a gel for containing the active ingredients of the present invention and delivering them to the oral cavity. Water is commonly used as a carrier material in oral compositions due to its many benefits. For example, water is useful as a processing aid, is benign to the oral cavity and assists in quick foaming of toothpastes. Water may be added as an ingredient in its own or it may be present as a carrier in other common raw materials such as, for example, sorbitol and sodium lauryl sulphate. The term total water content as used herein means the total amount of water present in the oral care composition, whether added separately or as a solvent or carrier for other raw materials but excluding that which may be present as water of crystallization in certain inorganic salts.

The oral care composition of the present invention comprises at least about 30% of a total water content. Preferably, the oral care composition comprises from more than about 35% to about 85% of a total water content. In other embodiments, the compositions comprise from about 40% to about 80%, alternatively from about 45% to about 75%, alternatively from about 50% to about 70%, alternatively from about 50% to about 60%, alternatively from about 45% to about 55%, alternatively from about 55% to about 65%, alternatively from about 65% to about 75%, alternatively combinations thereof, of a total water content.

Free of Abrasives

Preferably, the oral care composition of the present invention is substantially free of abrasives. The term "abrasive", for the purpose of present invention, includes calcium-containing abrasives and silica abrasives. The calcium-containing abrasives may be selected from the group consisting of calcium carbonate, dicalcium phosphate, tricalcium phosphate, calcium orthophosphate, calcium metaphosphate, calcium polyphosphate, calcium oxyapatite, sodium carbonate, and combinations thereof. In one embodiment where the calcium-containing abrasive is calcium carbonate, the calcium carbonate can be selected from the group consisting of fine ground natural chalk, ground calcium carbonate, precipitated calcium carbonate, and combinations thereof. The silica abrasives may generally have an average particle size ranging from 0.1 to 30 μm, and preferably from 5 to 15 μm. The silica abrasives can be precipitated silica or silica gels such as the silica xerogels marketed under the trade name "Syloid" by the W.R. Grace & Company, Davison Chemical Division and precipitated silica materials such as those marketed by the J.M. Huber Corporation under the trade name, Zeodent®, particularly the silicas carrying the designation Zeodent® 119, Zeodent® 118, Zeodent® 109 and Zeodent® 129.

Preferably, the oral care composition of the present invention contains low levels of abrasives. For example, the oral care composition may comprise from 0% to about 5% by weight of the composition, of abrasives, alternatively from 0% to about 3%, alternatively from 0% to 2%, alternatively from 0% to about 1%, alternatively less than about 3%, or less than about 2%, or less than about 1%, or less than about 0.5%, by weight of the composition. Preferably, the composition is substantially free of the abrasives, more preferably free of the abrasives.

Humectants

The oral care compositions herein may contain humectants. The humectants serve to keep the oral care composition from hardening upon exposure to air, to give a moist feel to the mouth, and, for particular humectants, to impart a desirable sweetness of flavor.

Suitable humectants for the present invention include edible polyhydric alcohols such as glycerin, sorbitol, xylitol, erythritol, butylene glycol, polyethylene glycol, propylene glycol, and combinations thereof. In one embodiment, the humectant is selected from sorbitol, glycerin, and combinations thereof. In another embodiment, the humectant is glycerin. In yet another embodiment, the humectant is sorbitol. In one embodiment, the oral care composition comprises from 1% to less than 50% of humectants by weight of the composition, preferably from 10% to 40%. In yet another embodiment, the oral care composition contains 15% to 30% of glycerin by weight of the oral care composition.

In some embodiments, the oral care composition of the present invention can comprise a polyol selected from the group consisting of glycerol, erythritol, xylitol, sorbitol, mannitol, and combinations thereof. Preferably the polyol is present in the amount of from 1% to 30%, preferably from 5% to 20%, by weight of the composition.

In one example, the oral care composition of the present invention is substantially free of ethanol, preferably essentially free of ethanol. The ethanol is not desirable, in some cases, as it may cause irritating feeling to the users.

Flavorant

The oral care compositions herein may comprise from about 0.001% to about 5%, alternatively from about 0.01% to about 4%, alternatively from about 0.1% to about 3%, alternatively from about 0.5% to about 2%, alternatively combination thereof, of a flavorant composition by weight of the oral care composition. The term flavorant composition is used in the broadest sense to include flavor ingredients, or sensates, or sensate agents, or combinations thereof. Flavor ingredients may include those described in U.S. Publication No. 2012/0082630A1 at paragraph 39; and sensates and sensate ingredients may include those described at paragraphs 40-45, incorporated herein by reference.

Examples of flavor compositions or flavor ingredients include: mint oils, wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, a-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, a-terpineol, linalool, limonene, citral, neral, geranial, geraniol nerol, maltol, ethyl maltol, anethole, dihydroanethole, carvone, menthone, beta -damascenone, ionone, gamma -decalactone, gamma -nonalactone, y-undecalactone, or combinations thereof. Generally suitable flavor ingredients are chemicals with structural features and functional groups that are less prone to redox reactions. These include derivatives of flavor ingredients that are saturated or contain stable aromatic rings or ester groups.

Sensates such as cooling, warming, and tingling agents are useful to deliver signals to the user. The most well-known cooling agent is menthol, particularly 1-menthol, which is found naturally in peppermint oil. Among synthetic cooling agents, many are derivatives of or are structurally related to menthol, i.e., containing the cyclohexane moiety, and derivatized with functional groups including carboxamide, ketal, ester, ether and alcohol. Examples include the p-menthanecarboxamide compounds such as N-ethyl-p-menthan-3-carboxamide (known commercially as "WS-3"). An example of a synthetic carboxamide cooling agent that is structurally unrelated to menthol is N,2,3-trimethyl-2-isopropylbutanamide. Additional exemplary synthetic cooling agents include alcohol derivatives such as 3-1-menthoxypropane-1,2-diol, isopulegol, p-menthane-3,8-diol; menthone glycerine acetal (known commercially as "MGA"); menthyl esters such as menthyl acetate, menthyl acetoacetate, menthyl lactate, and monomenthyl succinate.

Additional agents that are structurally unrelated to menthol but have been reported to have a similar physiological cooling effect include alpha-keto enamine derivatives described in U.S. Pat. No. 6,592,884, including 3-methyl-2-(1-pyrrolidinyl)-2-cyclopenten-1-one (3-MPC), 5-methyl-2-(1-pyrrolidinyl)-2-cyclopenten-1-one (5-MPC); 2,5-dimethyl-4-(1-pyrrolidinyl)-3(2H)-furanone (DMPF); icilin (also known as AG-3-5, chemical name 142-hydroxyphenyl]-4-[2-nitrophenyl]-1,2,3,6-tetrahydropyrimidine-2-one).

Some examples of warming agents include ethanol; nicotinate esters, such as benzyl nicotinate; polyhydric alcohols; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof.

Examples of some tingling agents include capsaicin; homocapsaicin, jambu oleoresin, zanthoxylum peperitum, saanshool-I, saanshool II, sanshoamide, piperine, piperidine, spilanthol, 4-(1-methoxymethyl)-2-phenyl-1,3-dioxolane, or combinations thereof.

The oral care compositions herein can further include herbal ingredients such as extracts of chamomile, oak bark, melissa, rosemary and salvia. These, and some of the herb-derived flavoring components can be included at levels just sufficient to provide a contribution to the flavor or they can be added at higher levels, such as 1% or more, in order to provide a greater therapeutic effect.

Preservatives

The oral care composition of the present invention may comprise preservatives. The preservatives may be benzyl alcohol, phenoxyethanol, sorbitan caprylate (Velsan SC®), 1-2 hexanediol & caprylyl glycol (Symdiol 68®), parabens and or combinations. The paraben may comprise methyl paraben or propyl paraben or combination thereof. Levels of benzyl alcohol or phenoxyethanol may be present in the amount of from greater than about 0.10% to about 0.40%, preferably from about 0.15% to about 0.30%, more preferably from about 0.17% to about 0.23%, alternatively from about 0.18% to about 0.22%, alternatively from about 0.19% to about 0.21%, alternatively about 0.20%, by weight of the composition. The levels of Velsan C® maybe present at the amount of from about 0.10% to about 0.50%, preferably about 0.20% to about 0.40%, more preferably alternatively from about 0.25% to about 0.30%. The level of Symdiol 68® maybe present from about 0.10% to about 0.80%, preferably about 0.10% to about 0.50% and more preferably from about 0.20% to about 0.30%. Levels of paraben may be present at the amount of about 0.01% to about 0.11%, preferably about 0.02% to about 0.10%, more preferably from about 0.03% to about 0.09%, by weight of the composition. In one embodiment, the composition 5 comprises from 0.005% to 0.1%, preferably from about 0.01% to about 0.08%, alternatively from about 0.01% to about 0.05%, of propyl paraben by weight of the composition. In another embodiment, the composition comprises from about 0.01% to about 0.1%, preferably from about 0.02% to about 0.07%, alternatively from about 0.03% to about 0.05%, of methyl paraben by weight of the composition.

In yet another embodiment, the paraben comprises a combination of methyl paraben and propyl paraben, wherein there is a greater weight ratio of methyl paraben to propyl paraben. In yet still another embodiment, the paraben is methyl paraben and propyl paraben, wherein the weight ratio of methyl paraben to propyl paraben is from about 5:3 to about 30:3, preferably greater than about 5:3 to about 20:3, more preferably from about 6:3 to about 15:3.

In one embodiment, the oral care compositions of the present invention are substantially free of triclosan (i.e., 5-chloro-2-(2,4-dichlorophenoxy)phenol), preferably free of triclosan.

Sweetener

The oral care compositions herein may include a sweetening agent. These include sweeteners such as saccharin, dextrose, sucrose, lactose, xylitol, maltose, levulose, aspartame, sodium cyclamate, D-tryptophan, dihydrochalcones, acesulfame, sucralose, neotame, and mixtures thereof. Sweetening agents are generally used in oral care compositions at levels of from about 0.005% to about 5%, alternatively from about 0.01% to about 1%, by weight of the composition, alternatively from about 0.1% to about 0.5%, alternatively combinations thereof.

Coloring Agents

The oral care compositions herein may include a coloring agent (i.e., pigments, dyes and opacifiers). The coloring agent may be in the form of an aqueous solution, preferably 1% coloring agent in a solution of water. Titanium dioxide may also be added to the present oral care composition. Titanium dioxide is a white powder which adds opacity to the oral care compositions. Titanium dioxide generally comprises from about 0.25% to about 5%, by weight of the composition. It will be appreciated that selected components for the compositions must be chemically and physically compatible with one another.

Anti-Calculus Agent

The oral care compositions may include an effective amount of an anti-calculus agent, which in one embodiment may be present from about 0.05% to about 50%, alternatively from about 0.75% to about 25%, alternatively from about 0.1% to about 15%. Non-limiting examples include those described in U.S. Publication No. 2011/0104081A1 at paragraph 64, and those described in U.S. Publication No. 2012/0014883A1 at paragraphs 63 to 68, as well as the references cited therein. One example is a pyrophosphate salt as a source of pyrophosphate ion. In one embodiment, the composition comprises tetrasodium pyrophosphate (TSPP) or disodium pyrophosphate or combinations thereof, preferably from about 0.01% to about 2%, more preferably from about 0.1% to about 1% of the pyrophosphate salt by weight of the composition. Without wishing to be bound by theory, TSPP may provide not only calcium chelating thereby mitigating plaque formation, but also may also provide the additional benefit of monofluorophosphate stabilization (in those formulations containing monofluorophosphate).

Other Ingredients

The present oral care composition may comprise other oral care active. For example, the oral care composition may further comprise a vitamin, where the vitamin is selected from Vitamin C, Vitamin E, Vitamin B5, and the combinations thereof. Herein the term "Vitamin" means said vitamin and all derivatives thereof. The ingredients may provide additional benefits to the oral care composition. The use of extracellular antioxidants, e.g. ascorbate or α-tocopherol, as chain breaking or radical scavenging antioxidants, helps control and modulate the intracellular reactive oxygen species (ROS) that can cause host-tissue damage. The use of dexpantheninaol can improve epithelialization and induce the proliferation phase in the wound healing of damaged tissue.

In some embodiments, the oral care composition may comprise from about 0.1% to about 10%, preferably from about 0.5% to about 8%, or from about 0.5% to about 5%, by weight of the composition, of vitamins selected from Vitamin C, Vitamin E, Vitamin B5, or the combinations thereof. The vitamins described in the present invention means said vitamins and all derivatives thereof.

The present oral care composition may further comprise the usual and conventional ancillary components such as surfactants, anti-microbial agents, fluoride ions, and other ingredients that are known to one skilled in the art. It will be appreciated that selected components for the oral care compositions must be chemically and physically compatible with one another.

Method of Use

The present invention also relates to methods for treating the oral cavity comprising applying to the intraoral tissue (e.g. oral mucosa, gingiva) of the oral cavity of a subject, particularly the gum tissue, leaving on for more than 2 minute, preferably more than 10 minutes, more preferably more than 30 minutes, or more than 60 minutes or longer. The method of use herein comprises contacting a subject's oral mucosa (e.g. gingival margin or gingival sulcus/pockets) with the oral care composition according to the present invention.

The present invention further relates to a method of improving Gum Health of a subject using the oral care composition described herein comprising the step of applying the oral care composition onto the intraoral tissue of the subject, preferably applying along the gingival margin or sulcus at least once a day, preferably at least twice a day, more preferably every time immediately after brushing teeth. The term "immediately" herein means within 1 hour, preferably within 30 minutes, more preferably within 15 minutes, alternatively within 10 minutes. Preferably, the oral care composition can be applied onto the intraoral tissue of the subject by using an applicator, which applicator has a handle and a head, to spread the oral care composition along the gingival margin or sulcus of the subject. Preferably, the oral care composition is dispensed on the head of the applicator before being applied onto the intraoral tissue.

The present invention further relates to a method of improving Gum Health of a subject, comprising at least two steps: (a) brushing teeth with an antibacterial toothpaste, preferably a stannous containing toothpaste, and immediately followed by (b) applying the oral are composition as defined herein onto the intraoral tissue of a subject, preferably applying along the gingival margin, sulcus or pockets.

TEST METHODS

Test 1: Rheological Test Method

A Rheological Test Method is described for assessing viscosity profile (and ran according to manufacturing instructions). The viscosity profiles are tested on a TA AR2000 rheometer (available from TA Instruments, New Castle, United States) by using Dentifrice Macro Rheology Test procedure. The geometry used is 40 mm steel parallel plate with solvent trap. Dentifrice is placed on the Peltier Plate of AR2000 rheometer and the Gap setting is 1000 micron. Dentifrice Macro Rheology Test consists of stress sweep oscillation, frequency sweep oscillation and steady state flow tests. The key parameter settings are listed: (a) Stress sweep step: Oscillation Stress (Pa): 0.01-500; (b) Frequency (Hz): 1.0; (c) Frequency sweep step: Frequency (Hz): 0.1-10, and Controlled Oscillation Stress (Pa): 1.5; (d) Steady state flow step 1: Shear rate ($s^{-1}$): 0.01-100; and (e) Steady state flow step 2: Shear rate ($s^{-1}$): 100-0.01.

Shear flow test is a viscosity testing mode to measure the viscosity at different shear rates. Steady state flow test is a flow in which the velocity at every point does not vary with time. The three main parameters in this test are viscosity, shear rate and shear stress. Power Law Model is a well-known model used to characterize the relationship between viscosity or shear stress and shear rate over the range of shear rates where shear thinning occurs in a Non-Newtonian fluid. It quantifies overall viscosity range and degree of deviation from Newtonian behavior. The Power Law Model is described as $\eta = K\gamma^{n-1}$, wherein $\eta$=viscosity and $\gamma$=shear rate. K is known as the Viscosity Consistency Coefficient, describing the overall range of viscosities across the part of the flow curve that is being modelled. The exponent "n" is known as the rate index. K and $\eta$ can be determined by Power Law Model fitting. Based upon rate index n, the Power Law Model describes three basic types of flow:

| | |
|---|---|
| n = 1 | Newtonian behavior |
| n < 1 | Shear thinning (or Pseudoplastic) |
| n > 1 | Shear thickening |

The viscosity profiles of the composition herein are represented by the Viscosity Consistency Coefficient K (Pa·s) determined by Power Law Model fitting with the shear rate range of 0.1-10 $s^{-1}$.

Test 2: Adhesiveness Test Method

The adhesiveness of samples is tested using Texture Analyser (TA Plus/30), Stable Micro System (Surrey, UK). The procedure is described as below:
1. Sample preparation: pipe out of gel or ointment sample from package as the amount of '0.03±0.005 g' to the test plate.
2. Make TA sequence to enable the instrument action: the probe is compressed into each sample, follow the determined programmed sequence (speed of 10 mm/sec, force of 5 g for stage 2; speed of 1 mm/sec, Force of 200 g for stage 4, and time is 1 sec for stage 5).
3. Instrument & accessory setting:
    3.1 Try the test with available probe options: metal round plate
    3.2 TA setting as 'compression'
4. All analyses should be performed on 5 replicates.
5. measurement: Adhesiveness: the work necessary to overcome the attractive forces between the surface of the sample and the surface of the probe.
6. Data calculation: Leverage programmed TTA data analysis macro (e.g. Force 5 g).

The adhesiveness values (unit: gf*sec) describes the energy necessary to overcome the attractive forces between the surface of the sample and the surface of the probe.

Test 3: Mucoadhesion Test Method

Mucoadhesion Test Method is provided. Test samples are labeled with Fluorescein isothiocyanate (FITC) at room temperature for 1 hour. The resulting solutions are dialyzed in phosphate buffered saline (PBS) for 48 h in order to remove the free FITC molecules. The silica wafers are treated with a mixture of ethanol/(3-Aminopropyl)triethoxysilane (APTES)/ammonia solution (20:4:1, v/v/v) for 8 hours and are then rinsed with ethanol and water, and dried to obtain the amine-functionalized silica wafers ($NH_2$-SW). $NH_2$-SW are incubated in mucin solution for 8 hours at room temperature. The mucin modified silica wafers are incubated with test sample in a PBS buffer in a shaker at 37° C. for 12 hours followed by rinsing with deionized water. The fluorescence images of the mucin modified silica wafers are taken by a fluorescence microscopy, and used for measurement of Fluorescent Intensity (FI) in ImageJ software (National Institutes of Health, USA, (https://imagej.nih.gov/ij/)). The Fluorescent Intensity Percentage ("FI %"), which is used to describe the "Mucoadhesion Index", is the fluorescent pixels relative to total pixels in a normalized image field. Therefore, a first test sample having a higher FI % has stronger mucoadhesion compared to a second test sample having a lower FI %.

Test 4: Assay for Measuring Improved Wound Healing of Human Gingival Fibroblasts In-vitro human gingival fibroblasts are used to assess the effects of wound healing migration as a result of treatment with the gel composition. The method involves three stages:

Stage 1—Culturing Primary Human Gingival Fibroblasts ("HGF")

Human gingival fibroblasts are collected from tooth extraction patients and washed with 5 mL of PBS (phosphate buffered saline). The tissue is chopped into small pieces and placed into 15 mL centrifuge tube. The samples are digested with equal amounts of 1 mL 8% dispase and 1 mL 6% collagenase for 1 hr at 37 ° C., during which time the samples need to be shaken every 15 minutes. Once the digestion process is complete, the tube is centrifuged at 1100 RPM for 6 minutes at room temperature. After centrifugation, a pellet of cells is formed in the bottom of the tube separating them from the supernatant solution. Then the supernatant is discarded and the cell pellet is suspended in 3 mL of fresh Minimum Essential Medium ("MEM", available from Thermo Fisher) culture media then transferred to a petri dish. The petri dish with cells are placed in the incubator at 37° C. with 5% $CO_2$ for about 10 days. The petri dish is checked for changes in media color every two days. Fresh culture media is replaced if changes in media color occurred.

Stage 2—Sub-Culturing Human Gingival Fibroblast

When there is 80-90% cell monolayer coverage of the petri dish, then the present culture media is removed and washed with 5 mL of PBS. 1 mL 0.25% trypsin-EDTA solution is added and the cells sit for about 1-2 minutes at 37° C. until the cells are visibly round-shaped. It may be necessary to tap the petri dish to remove any sticky cells from the petri dish surface. At least 1 mL of fresh MEM culture media is added to inactivate the trypsin and the cells are collected into a 15 mL centrifuge tube. The tube is then centrifuged at 1100 RPM for 6 minutes at room temperature. The supernatant is discarded and cell pellet is re-suspended in 4 mL of fresh MEM culture media in the same centrifuge tube. 4 petri dishes are each placed with 1 mL cell suspension and 9 mL fresh MEM culture media in the incubator at 37° C. with 5% $CO_2$ for about 3-5 days until 80-90% cell monolayer coverage on the petri dishes are observed. This stage should be repeated 2-4 times before the wound healing assay to achieve the highest cell viability.

Stage 3—Wound Healing Assay

When there is 80-90% cell monolayer coverage on the petri dishes, the present culture media is removed and washed with 5 mL of PBS. 1 mL 0.25% trypsin-EDTA solution is added and the cells sit for about 1-2 minute at 37° C. until the cells are visibly round-shaped. It may be necessary to tap the culture petri dish to remove any sticky cells from the petri dish surface. At least 1 mL of fresh MEM culture media is added to inactivate the trypsin and the cells are collected into a 15 mL centrifuge tube. The tube is then centrifuged at 1100 RPM for 6 minutes at room temperature. The supernatant is discarded and cell pellet is re-suspended in 6 mL of fresh MEM culture media. 1 mL cell suspension and 1 mL fresh MEM culture media are respectively added into each well of a 6-well plate. The plates are incubated at 37° C. with 5% $CO_2$ until 50-70% cell monolayer coverage is formed. The outer bottoms of wells are then marked with a line in middle as the reference line during image acquisition. A wound is created manually by scraping the right half of cell monolayer with a sterilized 1 mL pipette tip. The cells are washed with 2 mL PBS to remove any suspended cells until no suspended cells are visible. 2 mL culture media, and 2 ml culture media containing 1% Control Compositions or 2 mL culture media containing 1% Inventive Compositions are added to the wells.

High density digital images of the HGF are captured with an Olympus® IX71 digital SLR camera with an Olympus® UIS2 WHN10X objective lens. The first images are acquired at time 0 hr (i.e., Baseline) by using the middle line markings on the plates as a reference line. The plates are then incubated at 37° C. with 5% $CO_2$ for varying time intervals as described below. The matched photographed region is acquired as previously, and images are acquired at later time intervals (e.g., 16 hrs, 24 hrs, 48 hr, 65 hrs, 72 hrs, etc.) after baseline to assess the cell coverage (%) as an indication of the wound healing performance under the different treatment legs. Images are evaluated by Wimasis® WimScratch software (available from Wimasis GmbH, Germany) to determine the degree (i.e., percentage) of HGF cell coverage (i.e., wound healing) pass the marked wound boundary, as indicated by the dotted line, as compared to the matching baseline image for each sample. WimScratch software utilizes advanced edge detection and overlay techniques to recognize cells and blank area, i.e. the green overlay in the image represents the cell-covered area of the particular image and the grey area represents the wound area. The readout is presented for both area and is normalized as percent of total area.

EXAMPLES

The following examples and descriptions further clarify embodiments within the scope of the present invention. These examples are given solely for the purpose of illustration and are not to be construed as limitations of the present invention as many variations thereof are possible without departing from the spirit and scope.

Example A: Examples 1 to 4

Example 1 to 4 are gel compositions shown in Table 1 below with amounts of components in wt %. They may be suitably prepared by conventional methods chosen by the formulator. Examples 1 to 4 are inventive formulations according to the present invention, made with sodium hyaluronate and combinations of at least two polymers, with or without allantoin.

TABLE 1

Gel Composition Examples 1 to 4

| Ingredients | Amount (wt %) | | | |
| --- | --- | --- | --- | --- |
| | Example 1 | Example 2 | Example 3 | Example 4 |
| Glycerin | 20 | 20 | 20 | 20 |
| Propyl Paraben | 0.03 | 0.03 | 0.03 | 0.03 |
| Xylitol | 2 | 2 | 2 | 2 |
| Sodium Saccharin | 0.1 | 0.1 | 0.1 | 0.1 |
| Sodium Hydroxide (50%) | 0.9 | 0.9 | 0.9 | 0.9 |
| PEG 300 | 0.5 | 0.5 | 0.5 | 0.5 |
| Carbomer | 1.5 | 1.5 | 1.5 | 1.5 |
| PVPK90 | 1.5 | 1.5 | 1.5 | 1.5 |
| Sodium Hyaluronate | 0.21 | 0.21 | 0.526 | 0.526 |
| Allantoin | 0 | 0.1 | 0 | 0.1 |
| Panthenol (powder) | 0.5 | 0.5 | 0.5 | 0.5 |
| Tocopherol Acetate | 0.5 | 0.5 | 0.5 | 0.5 |
| Sodium Ascorbyl Phosphate | 0.91 | 0.91 | 0.92 | 0.92 |
| Sodium Pyrophosphate | 0.5 | 0.5 | 0.5 | 0.5 |
| Preservatives | 0.15 | 0.15 | 0.15 | 0.15 |
| Flavorant | 1.03 | 1.03 | 1.03 | 1.03 |
| Water & Minors (e.g. Coloring Agent) | Q.S. | Q.S. | Q.S. | Q.S. |
| Total | 100 | 100 | 100 | 100 |

*Sodium hyaluronate having M.W. of ~1,400,000 Da.

Example B: Assay for Measuring Improved Wound Healing of Human Gingival Fibroblasts In-vitro human gingival fibroblasts are used to assess the effects of wound healing migration as a result of treatment with Inventive Compositions and Control Compositions. The method involves three stages:

Stage 1—Culturing Primary Human Gingival Fibroblasts ("HGF")

Human gingival fibroblasts are collected from tooth extraction patients and washed with 5 mL of PBS (phosphate buffered saline). The tissue is chopped into small pieces and placed into 15 mL centrifuge tube. The samples are digested with equal amounts of 1 mL 8% dispase and 1 mL 6% collagenase for 1 hr at 37° C., during which time the samples need to be shaken every 15 minutes. Once the digestion process is complete, the tube is centrifuged at 1100 RPM for 6 minutes at room temperature. After centrifugation, a pellet of cells is formed in the bottom of the tube separating them from the supernatant solution. Then the supernatant is discarded and the cell pellet is suspended in 3 mL of fresh Minimum Essential Medium ("MEM", available from Thermo Fisher) culture media then transferred to a petri dish. The petri dish with cells are placed in the incubator at 37° C. with 5% $CO_2$ for about 10 days. The petri dish is checked for changes in media color every two days. Fresh culture media is replaced if changes in media color occurred.

Stage 2—Sub-Culturing Human Gingival Fibroblast

When there is 80-90% cell monolayer coverage of the petri dish, then the present culture media is removed and washed with 5 mL of PBS. 1 mL 0.25% trypsin-EDTA solution is added and the cells sit for about 1-2 minutes at 37° C. until the cells are visibly round-shaped. It may be necessary to tap the petri dish to remove any sticky cells from the petri dish surface. At least 1 mL of fresh MEM culture media is added to inactivate the trypsin and the cells are collected into a 15 mL centrifuge tube. The tube is then centrifuged at 1100 RPM for 6 minutes at room temperature. The supernatant is discarded and cell pellet is re-suspended in 4 mL of fresh MEM culture media in the same centrifuge tube. 4 petri dishes are each placed with 1 mL cell suspension and 9 mL fresh MEM culture media in the incubator at 37° C. with 5% $CO_2$ for about 3-5 days until 80-90% cell monolayer coverage on the petri dishes are observed. This stage should be repeated 2-4 times before the wound healing assay to achieve the highest cell viability.

Stage 3—Wound Healing Assay

When there is 80-90% cell monolayer coverage on the petri dishes, the present culture media is removed and washed with 5 mL of PBS. 1 mL 0.25% trypsin-EDTA solution is added and the cells sit for about 1-2 minute at 37° C. until the cells are visibly round-shaped. It may be necessary to tap the culture petri dish to remove any sticky cells from the petri dish surface. At least 1 mL of fresh MEM culture media is added to inactivate the trypsin and the cells are collected into a 15 mL centrifuge tube. The tube is then centrifuged at 1100 RPM for 6 minutes at room temperature. The supernatant is discarded and cell pellet is re-suspended in 6 mL of fresh MEM culture media. 1 mL cell suspension and 1 mL fresh MEM culture media are respectively added into each well of a 6-well plate. The plates are incubated at 37° C. with 5% $CO_2$ until 50-70% cell monolayer coverage is formed. The outer bottoms of wells are then marked with a line in middle as the reference line during image acquisition. A wound is created manually by scraping the right half of cell monolayer with a sterilized 1 mL pipette tip. The cells are washed with 2 mL PBS to remove any suspended cells until no suspended cells are visible. 2 mL culture media, and 2 ml culture media containing 1% Control Compositions or 2 mL culture media containing 1% Inventive Compositions are added to the wells.

High density digital images of the HGF are captured with an Olympus® IX71 digital SLR camera with an Olympus® UIS2 WHN10X objective lens. The first images are acquired at time 0 hr (i.e., Baseline) by using the middle line markings on the plates as a reference line. The plates are then incubated at 37° C. with 5% $CO_2$ for varying time intervals as described below. The matched photographed region is acquired as previously, and images are acquired at later time intervals (e.g., 16 hrs, 24 hrs, 48 hr, 65 hrs, 72 hrs, etc.) after baseline to assess the cell coverage (%) as an indication of the wound healing performance under the different treatment legs. Images are evaluated by Wimasis® WimScratch software (available from Wimasis GmbH, Germany) to determine the degree (i.e., percentage) of HGF cell coverage (i.e., wound healing) pass the marked wound boundary, as indicated by the dotted line, as compared to the matching baseline image for each sample. WimScratch software utilizes advanced edge detection and overlay techniques to recognize cells and blank area, i.e. the green overlay in the image represents the cell-covered area of the particular image and the grey area represents the wound area. The readout is presented for both area and is normalized as percent of total area.

Results: Table 1 shows cell recovery rate of HGF 72 hrs post-treatment with the Composition Ex. 1 (i.e., 0.2% HA only) and Composition Ex. 2 (i.e., 0.2% HA+0.1% Allantoin). With reference to Table 2, the results show that the Inventive Composition Ex. 1 containing 0.2% HA improves the wound healing by increasing cell coverage from 22.5% to 32.2% of the wound area. Meanwhile, the Composition Ex. 2 containing 0.2% HA and 0.1% allantoin improves the wound healing by increasing cell coverage even further to 60.3% of the wound area.

TABLE 2

| Treatment | Cell coverage of the wound area 72 hrs post-treatment |
| --- | --- |
| No treatment | 22.5% |
| Composition Ex. 1 | 32.2% |
| Composition Ex. 2 | 60.3% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A leave-on oral care composition comprising:
   a) from about 0.1% to about 10%, by weight of the composition, of a hyaluronic acid or a salt thereof, wherein the hyaluronic acid has a weight average molecular weight of from about 900,000 Daltons to about 2,000,000 Daltons;
   b) from about 0.5% to about 10%, by weight of the composition, of a polyacrylic acid;
   c) from about 0.5% to about 10%, by weight of the composition, of an additional polymer, wherein the additional polymer does not include an anionic cellulose; and
   d) from about 30% to about 75%, by weight of the composition, of total water content.

2. The leave-on oral care composition of claim 1, wherein the hyaluronic acid is present in an amount of from about 0.1% to about 5%, by weight of the composition.

3. The leave-on oral care composition of claim 1, wherein the polyacrylic acid is present in the amount of from about 0.5% to about 5%, by weight of the composition.

4. The leave-on oral care composition of claim 1, further comprising from about 0.01% to about 5%, by weight of the composition, of allantoin.

5. The leave-on oral care composition of claim 1, wherein the additional polymer is selected from the group consisting of natural gum, linear sulfated polysaccharide, nonionic cellulose derivative, co-polymers of maleic anhydride with methyl vinyl ether, polyvinyl pyrrolidine, and combinations thereof.

6. The leave-on oral care composition of claim 5, wherein the additional polymer is present in the amount of from about 0.2% to about 10%, by weight of the composition.

7. The leave-on oral care composition of claim 5, wherein the additional polymer is selected from the group consisting of xanthan gum, carrageenan, hydroxyethyl cellulose, hydroxypropyl cellulose, hydroxymethyl cellulose, co-polymers of maleic anhydride with methyl vinyl ether having a weight average molecular weight of about 30,000 Daltons to about 1,000,000 Daltons, polyvinyl pyrrolidine, and combinations thereof.

8. The leave-on oral care composition of claim 1, further comprising a polyol selected from the group consisting of glycerol, erythritol, xylitol, sorbitol, mannitol, and combinations thereof.

9. The leave-on oral care composition of claim 8, wherein the polyol is present in the amount of from about 1% to about 30%, by weight of the composition.

10. The leave-on oral care composition of claim 1, further comprising a vitamin selected from the group consisting of Vitamin C, Vitamin E, Vitamin B5, and combinations thereof.

11. The leave-on oral care composition of claim 1, wherein the total water content is from about 40% to about 75%, by weight of the composition.

12. The leave-on oral care composition of claim 1, wherein the oral care composition is in a gel form.

13. The leave-on oral care composition of claim 1, wherein the oral care composition is substantially free of abrasives.

14. A method of improving gum health of a subject, the method comprising the steps of applying the leave-on oral care composition of claim 1 onto intraoral tissue of the subject, and leaving the oral care composition on the intraoral tissue a duration of time of from about 1 minute to about 1000 minutes.

15. The method of claim 14, wherein the applying step is conducted as a last step of an oral hygiene regimen.

16. The method of claim 14, wherein the leave-on oral care composition is applied onto the intraoral tissue of the subject with an applicator comprising a handle and a head to spread the oral care composition onto the intraoral tissue of the subject.

17. A method of improving gum health of a subject, the method comprising the steps of:
   (a) brushing teeth of the subject with an antibacterial toothpaste; and
   (b) subsequently, applying the leave-on oral care composition of claim 1 onto intraoral tissue of the subject, and leaving the oral care composition on the intraoral tissue for a duration of time of from about 1 minute to about 1000 minutes.

18. The method of claim 17, wherein the oral care composition is applied onto the intraoral tissue of the subject with an applicator comprising a handle and a head to spread the oral care composition onto the intraoral tissue of the subject.

19. A kit comprising a toothpaste and the leave-on oral care composition of claim 1.

20. A kit comprising the leave-on oral care composition of claim 1 and a delivery carrier, wherein the delivery carrier comprises strip, film of material, dental tray, aligner, sponge material, applicator, or mixtures thereof.

* * * * *